United States Patent [19]

Loud et al.

[11] 3,992,523

[45] Nov. 16, 1976

[54] PENICILLIUM-TYPE MOLDS AND ANTIMICROBIAL DERIVATIVES THEREFROM

[75] Inventors: Norman D. Loud, Clearwater, Fla.; H. Damon Swanson, Concord, N.H.; Robert H. Rines, Boston, Mass.

[73] Assignee: Allor Foundation, Belmont, Mass.

[22] Filed: June 4, 1975

[21] Appl. No.: 583,537

Related U.S. Application Data

[63] Continuation of Ser. No. 439,438, Feb. 4, 1974, abandoned.

[52] U.S. Cl. .............................. 424/114; 195/36 P; 195/81; 424/115
[51] Int. Cl.² ...................... C12D 9/06; A61K 35/70
[58] Field of Search ............. 195/36 P, 81; 424/114, 424/115

[56] References Cited
UNITED STATES PATENTS 2,445,748   7/1948   Demerec ........................... 195/36 P

*Primary Examiner*—Alvin E. Tanenholtz
*Attorney, Agent, or Firm*—Rines and Rines

[57] ABSTRACT

This disclosure deals with novel man-induced molds of the pencillium type found, however, to have both gram positive and gram negative antimicrobial effects, which effects have further been discovered to be synergistically enhanced in mixed culture.

7 Claims, 10 Drawing Figures

PENICILLIUM-TYPE

This is a continuation application of Ser. No. 439,438, filed Feb. 4, 1974, now abandoned.

The present invention relates to penicillium-type molds, cultures, organisms, strains and other derivatives therefrom, hereinafter sometimes referred to generically as "molds".

More specifically, in summary, the invention embraces such newly discovered molds which have been recovered for the first time from plant material, "Artemisia." The molds have been found to exhibit antimicrobial effects against both gram positive and gram negative organisms, and a surprising synergistic enhancement of such effects in mixed culture.

Penicillium molds have been recovered from other materials, as described, for example, in U.S. Pat. Nos. 3,625,826; 3,699,097; 3,716,454; 3,717,548; 3,736,230; 3,749,711; and such have been known to exhibit antimicrobial effects against certain gram positive bacteria.

An object of the present invention, however, is to provide new antimicrobial molds and synergistic combinations of the same that can provide a wide spectrum of both gram positive and gram negative antimicrobial effects and the like.

A further object is to provide new and improved penicillium-type antimicrobial molds, antibiotic substances produced therefrom, and techniques for developing the same, of more general applicability, also.

An additional object is to provide the hereinafter described new molds, termed *Penicillium rineseum* and *Penicillium allorenses*, and culture combinations of the same.

Other and further objects will be explained hereinafter and are more particularly delineated in the appended claims.

The invention will now be described with reference to the accompanying drawings, FIG. 1 of which is a photograph (approximately one-half size reduction) of one of the molds of the invention, *Penicillium rineseum*, incubated on Czapek solution agar, as later detailed;

FIG. 2 is a similar photograph of the mold *Penicillium allorensis* of the invention, similarly incubated on Czapek solution agar;

FIG. 3 is a similar photograph of known *Penicillium chrysogenum*, similarly incubated on Czapek solution, obtained from "A Manual of the Penicillia", K. B. Raper, et al., Hafner Publishing Company, 1968, p. 360;

Figure 1:
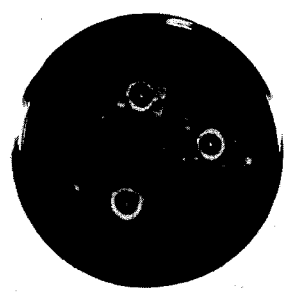

It is first in order to describe the method or technique for recovering the molds of the invention from the above-mentioned plant material. The molds were isolated after having steeped the dried plant material in boiling distilled water. Closed, but not airtight, flasks of steeped material were then incubated at room temperature for 1 week to allow for mycelial growth on the liquid's surface. Portions of the molds were then transferred with a sterile loop from the plant extract to agar mediums and incubated further at 22° and 37° C. The two resulting species *Penicillium rineseum* and *Penicillium allorensis* were then readily separated into pure culture because of diverse colony characteristics, later discussed.

For cultural and morphological identification, the *Penicillium* species were grown on Czapek's solution agar, as described by Dox, A. W., 1909, Intracellular enzymes of lower fungi, especially those of *Penicillium camemberti*, Journal of Biological Chemistry, 7, 461–467; malt extract agar, and Sabouraud agar modified. Czapek's solution agar contained (w/v): $NaNO_3$, 0.3%; $MgSO_4.7H_2O$, 0.05%; $K_2HPO_4$, 0.1%; $KCl$, 0.05%; $FeSO_4.7H_2O$, 0.001%; sucrose, 3%; and agar, 1.5%. Measurements of antimicrobial activity were conducted with Mueller Hinton Medium (Difco).

Microscopic and macroscopic observations were conducted with the isolates in the manner described by Raper, K. B., and Thom. C., *A Manual of the Penicillia*, New York: Hafner Publishing Co. Both in situ and mounted samples were microscopically observed for morphological characteristics. At the macroscopic level, the species were planted on agar mediums noted above, and cultural characteristics observed during a 2 week interval. Of principal interest were colony size, shape, texture, and color and reverse side characteristics.

The molds were tested for antimicrobial activity after 3 weeks incubation at 22° C on Czapek's solution agar and malt extract agar. The agar-plug technique used, was that described by Raper et al, supra, and Fusaro, R. M., 1972, Inoculation technique for fungus cultures, Journal of Applied Microbiology, 23, 174–176. A selected colony was incised and a plug of agar (6mm), containing both that portion of the colony and agar, were removed. The agar plug was then placed on the surface of a Mueller Hinton Medium plate which had previously been inoculated, by swabbing, with one of the test microorganisms. The plate was then incubated for 24 hours at 37° C and zones of inhibition, in millimeters, measured.

The morphological characteristics of each of the two new species are not readily distinguishable and speciation is correlated with marked cultural and biochemical dissimilarities.

TABLE 1

Morphological characteristics of *Penicillium rineseum* and *Penicillium allorensis*

Penicillius . . . typcial of the genus Penicillium; single verticil, 6–8 metulae 10–11 $\mu$ in length.

Condiophores and sterigmata . . . characteristic of Bi-
uerticillataSymmetrica; lanceolate sterigmata 10–11
$\mu$ by $2\mu$.
Conidia . . . smooth walled, elliptical, $4\mu$ on long axis.
Perithecium . . . absent.
Sclerotium . . . absent.

Cultural characteristics of the new species are compared with two known species of Penicillium, *Penicillium chrysogenum* and *Penicillium variabile*, which is the closest known Penicillium to that of the present invention. The species of the invention, however, have been found to be both biochemically and culturally distinct, as detailed in the following Table 2, referring to the photographs of the drawings.

culture growth on the same agar medium results in a synergistic increase in efficacy, including inhibition of growth of *Pseudomonas aeruginosa*.

*Penicillium chrysogenum*, on the other hand, known to produce the antibiotic penicillin, is observed to be limited in its spectrum of activity by exhibiting no antimicrobial properties against gram negative bacteria.

A search of the literature has not revealed antimicrobial properties of *Penicillium variabile*. This fungal microorganism has been taxonomically placed within the rugulosum series ("Antibiotic-Producing Microscopic Fungi", V. I. Bilai, Elsevier Publishing Company, 1963, p. 215); however, it has similarly been placed within the purpurogenum series (Raper, et al., supra, p. 631).

TABLE 2

Cultural characteristics of *Penicillium rineseum* and
*Penicillium allorensis* incubated 14 days at 22° C on Czapek
solution agar, malt extract agar and Sabouraud agar modified. Comparison with *Penicillium chrysogenum* and *Penicillium variable*.

Figure 2:
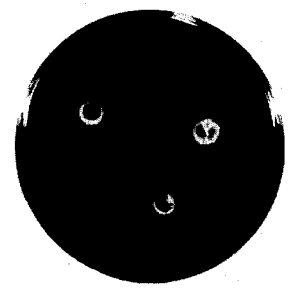
Figure 3:
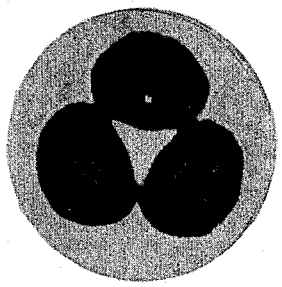
Figure 4:
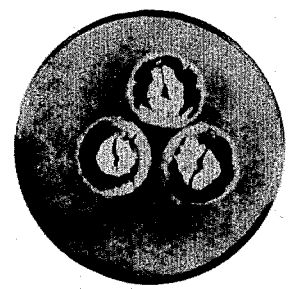
FIG. 4 is a similar photograph of known *Penicillium variabile*, similarly incubated on Czapek solution agar, obtained from p. 640 of the said Raper et al. text.
Figure 5:
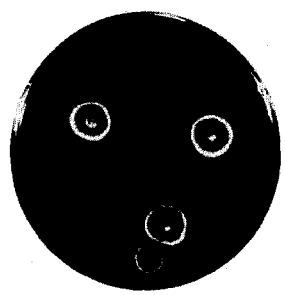
FIG. 5 is a similar photograph of the *Penicillium rineseum* of the invention incubated on malt extract agar as later detailed.
Figure 6:
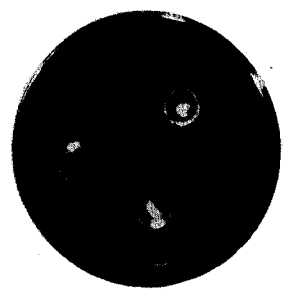
FIG. 6 is a similar photograph of the *Penicillium allorensis* of the invention, similarly incubated on malt extract agar.
Figure 7:
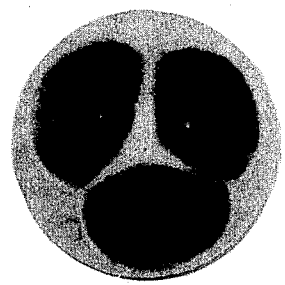
FIG. 7 is a similar photograph of known *Penicillium chrysogenum*, similarly incubated on malt extract agar, obtained from p. 360 of the Raper et al. text.
Figure 8:
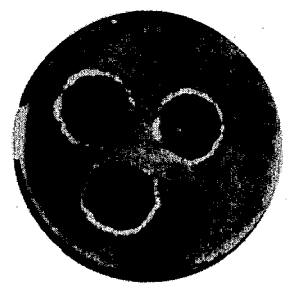
FIG. 8 is a similar photograph of known *Penicillium variabile*, similarly incubated on malt extract of agar, obtained from p. 640 of the Raper et al. text.
Figure 9:
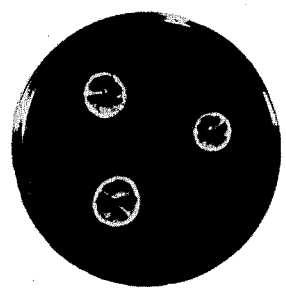
FIG. 9 is a similar photograph of the *Penicillium rineseum* of the invention incubated on Sabouraud agar modified, as later detailed.
Figure 10:
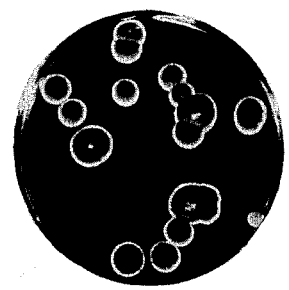
FIG. 10 is a similar photograph of the *Penicillium allorensis* of the invention, similarly incubated on Sabouraud agar modified.

|  | *Penicillium rineseum* | *Penicillium allorensis* |
|---|---|---|
| Czapek's solution (See FIG. 1) | 2 cm diameter; velvety; yellow umbo surrounded by green, in turn surrounded by yellow, and white margin; reverse white and cream mix with trace of orange; small amount of exudate; no soluble pigment; no odor; | 1.5–2 cm diameter; velvety; mottled overall with green, white and yellow radially furrowed; reverse cream with trace of orange; small amount of exudate no soluble pigment; no odor. (See FIG. 2) |
| Malt extract agar (See FIG. 5) | 1.5–2 cm diameter; overall blue-green with heavy (mealy) sporing; submerged (non-sporing) hyphae in margin; reverse olive green with bright orange center; no soluble pigment, no odor; | 1.5–2 cm diameter; overall blue-green with white patches and heavy sporing (mealy); white tufted central umbo; heavy sporing arising from submerged margin; reverse olive green with bright orange center; no soluble pigment; no odor. (See FIG. 6) |
| Sabouraud agar (See FIG. 9) | 2–3 cm diameter; overall blue-green with yellow patches; deep radial furrows; white margin; large amount of clear exudate; reverse cream with trace of red; no soluble pigment; no odor. | 2–3 cm diameter; overall blue-green; central umbo; light radial furrows; slight amount of exudate; blue-green hyphae arising from submerged margin; reverse white to cream; no soluble pigment; no odor. (See FIG. 10) |
|  | *Penicillium chrysogenum*[1] | *Penicillium variabile*[2] |
|  | 4.5 to 5.0 cm diameter; felt-like, velvety, loose texture; conspicious radial furrows with no apparent umbo; yellowish to greenish shades with no white and no apparent margin; reverse bright to dull yellow; abundant exudate; odor lacking to indefinite, (See FIG. 3) | 2.5–3 diameter; velvety or slightly granular; radial furrows with no apparent umbo; bright yellow to cream yellow to orange buff shades with white to yellow margin; reverse yellow to orange-brown; exudate lacking or limited; odor not pronounced; no soluble pigment. (See FIG. 4) |
|  | 5.5 to 6.0 cm diameter; same color as in Czapek solution, with no radial or other furrows; narrow white to yellowish margin; reverse dull yellow shades (See FIG. 7) | 3.0 to 3.5 cm diameter; dull yellow green to gray-green shades with plane surface or lightly furrowed; no central umbo; yellow encrusted mycelium in marginal and submarginal areas; indistinct odor. (See FIG. 8) |
|  | Information not available in published form. | Information not available in published form. |

[1]From "A Manual of the Penicillia", K. B. Raper, et al., Hafner Publishing Company, 1968, p. 359–361.
[2]From "A Manual of the Penicillia", K. B. Raper, et al., Hafner Publishing Company, 1968, p. 642–643.

While, as shown in Table 2, culture characteristics of the two new species, when each is considered independently, impart some resemblances to the known species *Penicillium variabile*, an overall analysis of colony properties, (e.g., shape and color, sporing phenomenon, reverse side characteristics and absence of odor, etc.), provides a distinct pattern for speciation.

New performance results were discovered, moreover, regarding antimicrobial properties of the new species and particularly of the antibiotic substances produced therefrom. *Penicillium allorensis*, grown on Czapek solution agar, produces an antibiotic that exhibits the greater spectrum of activity against both gram positive and gram negative bacteria. Antimicrobial activity of *Penicillium rineseum*, grown on the same medium to produce an antibiotic substance, is effective against gram positive population of bacteria. A mixed An antibiotic of the rugulosum series, called rugulosin, is found to show weak activity against gram negative bacteria, but to be strongly active against Streptoccus, Corynebacterium, and Bacillus and only weakly active against Straphylococcus ("Antibiotics II", T. Korzybski, et al., Pergamon Press, 1967).

For these tests, the molds were incubated for 21 days at room temperature in pure culture on Czapek's solution agar and malt extract agar and in mixed culture on malt extract agar. Antimicrobial activity was tested by planting a portion (plug) of the agar medium onto an inoculated Mueller Hinton agar plate, as before mentioned. Both molds elicited diverse activity when grown in pure culture on Czapek's solution agar; that of allorensis giving the greater spectrum. The only resistant bacterium of those tested was *Pseudomonas aeruginosa*. Activity was limited in both pure culture variants when the growth medium was malt extract agar. Of the six test microorganisms, both gram positive and negative, only *Staphylococcus aureus* and *Bacillus cereus* were sensitive. However, when a mixed culture was employed on malt extract agar, there occurred a synergistic reaction where all but one test organism, *Salmonella paratyphi* B, were affected. The mixed culture technique was the only condition whereby activity could be shown against *Ps. aeruginosa* in these tests.

Seven examples of such antimicrobial tests are presented below, each for five further exemplary applications: two sets of tests with *Penicillium rineseum;* two sets with *Penicillium allorensis;* and one set with the combination of the two species.

Examples 1 through 7 of tests of Antibacterial properties of the *Penicillium rineseum* and *Penicillium allorensis* against a spectrum of gram positive and gram negative bacteria.

|  | P. rineseum[1] | P. allorensis[1] | P. rineseum[2] and P. allorensis | P. rineseum[3] | P. allorensis[3] | P. chrysogenum[4] |
|---|---|---|---|---|---|---|
| Example 1 |  |  |  |  |  |  |
| Staphylococcus aureus | + | + | + | − | + | + |
| Example 2 |  |  |  |  |  |  |
| Salmonella paratyphi B | − | − | − | + | + | − |
| Example 3 |  |  |  |  |  |  |
| Bacillus subtilis − | − | + | + | + | − |  |
| Example 4 |  |  |  |  |  |  |
| Pseudomonas aeruginosa | − | − | + | − | − | − |
| Example 5 |  |  |  |  |  |  |
| Serralla marcesens | − | − | + | − | + | − |
| Example 6 |  |  |  |  |  |  |
| Escherichia coli | − | − | + | − | + | − |
| Example 7 |  |  |  |  |  |  |
| Bacillus cereus | + | + | + | + | + | + |

[1]*Penicillium rineseum* and *Penicillium allorensis* grown in pure culture on malt extract agar.
[2]*Penicillium rineseum* and *Penicillium allorensis* grown in mixed culture on malt extract agar.
[3]*Penicillium rineseum* and *Penicillium allorensis* grown in pure culture on Czapek solution agar.
[4]From "A Manual of the Penicillia", K. B. Raper, et al., Hafner Publishing Company, 1968, p. 89–101.
(+) refers to positive antibacterial activity.
(−) refers to negative antibacterial activity.

The species of the invention, *Penicillium rinesium* and *Penicillium allorensis*, have been deposited at the American Type Culture Collection under accession number ATCC No. 20398 and No. 20399, respectively.

What is claimed is:

1. A method of producing an antibiotic, comprising incubating molds selected from the group consisting of *Penicillium rinesium* and *Penicillium allorensis* on an aqueous nutrient medium until substances having substantial antimicrobial activity are produced, and then recovering said substances from said medium.

2. A method of producing an antibiotic, comprising incubating in mixed culture the molds *Penicillium rinesium* and *Penicillium allorensis* on an aqueous nutrient medium until substances having substantial antimicrobial activity are produced, and then recovering said substances from said medium.

3. A method of inhibiting the activity of at least one of *Staphylococcus aureus* and *Bacillus cereus* bacteria, which comprises subjecting the bacteria to the antimicrobial acitivity of a substance produced from the mold *Penicillium rinesium* grown on malt extract agar.

4. A method of inhibiting the activity of at least one of *Salmonella paratyphi* B, *Bacillus subtilis*, and *Bacillus cereus* bacteria, which comprises subjecting the bacteria to the antimicrobial activity of a substance produced from the mold *Penicillium rinesium* grown on Czapek's solution agar.

5. A method of inhibiting the activity of at least one of *Staphylococcus aureus* and *Bacillus cereus* bacteria, which comprises subjecting the bacteria to the antimicrobial activity of a substance produced from the mold *Penicillium allorensis* grown on malt extract agar.

6. A method of inhibiting the activity of at least one of *Staphylococcus aureus*, *Salmonella paratyphi* B, *Bacillus subtilis*, *Serratia marcesens*, *Escherichia coli*, and *Bacillus cereus* bacteria, which comprises subjecting the bacteria to the antimicrobial activity of a substance produced from the mold *Penicillium allorensis* grown on Czapek's solution agar.

7. A method of inhibiting the activity of at least one of *Staphylococcus aureus*, *Bacillus subtilis*, *Pseudomonas aeruginosa*, *Serratia marcesens*, *Escherichia coli*, and *Bacillus cereus* bacteria, which comprises subjecting the bacteria to the antimicrobial activity of substances grown from the molds *Penicillium rinesium* and *Penicillium allorensis* in mixed culture on malt extract agar.

* * * * *